United States Patent [19]

Gillies et al.

[11] Patent Number: 4,916,533

[45] Date of Patent: Apr. 10, 1990

[54] ENDOSCOPE INSERTION DIRECTION DETECTING METHOD

[75] Inventors: Duncan F. Gillies; Gul N. Khan, both of London, England

[73] Assignee: Olympus Optical Co., Ltd., Tokyo, Japan

[21] Appl. No.: 330,523

[22] Filed: Mar. 30, 1989

[30] Foreign Application Priority Data

Dec. 31, 1988 [GB] United Kingdom ................. 8830465

[51] Int. Cl.⁴ ........................... A61B 1/04; A61B 1/06
[52] U.S. Cl. ............................................ 358/98; 128/6
[58] Field of Search ............................... 358/98; 128/6

[56] References Cited

U.S. PATENT DOCUMENTS 4,834,070  5/1989  Saitou ..................................... 128/6

Primary Examiner—Howard W. Britton
Attorney, Agent, or Firm—Armstrong, Nikaido, Marmelstein, Kubovcik & Murray

[57] ABSTRACT

The endoscope insertion direction detecting method is to extract the form of a fold existing on the inside wall of an observed part from an endoscope picture image and to judge the direction of inserting the endoscope on the basis of the form of this fold and comprises, for example, a step of extracting discontinuous points in the endoscope picture image, a step of extracting line segments based on the above mentioned discontinuous points from respective divided picture images obtained by dividing into a plurality of picture images the picture image obtained by the step of extracting the discontinuous points, a step of connecting the line segments obtained by the step of extracting the line segments and a step of considering the line connected by the connecting step to be the form of a fold existing on the inside wall of the observed part and judging the endoscope insertion direction on the basis of this form of the fold. The step of extracting the discontinuous points includes, for example, extracting points at which the brightness and color of the picture image varies. The step of extracting the line segments has, for example, a step of extracting line segment candidates and a step of extracting the optimum line segment from among the candidates extracted by this candidate extracting step.

21 Claims, 18 Drawing Sheets

| −1 | 0 | 1 |
|---|---|---|
| $-\sqrt{2}$ | 0 | $\sqrt{2}$ |
| −1 | 0 | 1 |

| 1 | $\sqrt{2}$ | 1 |
|---|---|---|
| 0 | 0 | 0 |
| −1 | $-\sqrt{2}$ | −1 |

| NAME | | ARRANGED ELEMENTS | NUMBER OF VOTES |
|---|---|---|---|
| LINE | 1 | (4, 18) | 12 |
| " | 2 | (4, 26) | 8 |
| " | 3 | (5, 7) | 11 |
| " | 4 | (16, 4) | 9 |
| " | 5 | (19, 10) | 12 |

△,× --- EDGE POINT (△ ----- EDGE POINT BY NOISE)

EXAMPLE $\theta$ = 5°  
  8°  
  20°  
  21°  
  22° } GROUP 1  
  23°  
  29°  
  35°  
  62° ----- GROUP 2

```
EXAMPLE
 ( 1, 8 )
 ( 1, 7 )
 ( 2, 7 )
 ( 2, 6 )
 ( 2, 4 )     ← △y > 1
 ( 3, 4 )
 ( 3, 3 )
 ( 3, 2 )
 ( 3, 1 )
 ( 4, 1 )
```

FIG.23

| POINT | CONTINUITY | GRAY LEVEL | EDGE ORI. | GROUP |
|---|---|---|---|---|
| 1 | GROUP 1 | GROUP a | GROUP α | A |
| 2 | " 1 | " a | " α | A |
| 3 | " 1 | " a | " α | A |
| 4 | " 1 | " a | " α | A |
| 5 | " 1 | " a | " α | A |
| 6 | " 1 | " a | " α | A |
| 7 | " 1 | " b | " α | B |
| 8 | " 1 | " b | " α | B |
| 9 | " 2 | " b | " α | C |
| 10 | " 3 | " a | " β | D |
| 11 | " 4 | " c | " β | E |
| 12 | " 4 | " c | " γ | F |

ENDOSCOPE INSERTION DIRECTION DETECTING METHOD

BACKGROUND OF THE INVENTION

1. Field of the Invention

This invention relates to methods of detecting the direction of insertion of an endoscope and more particularly to an endoscope insertion direction detecting method adapted to automatically inserting an endoscope in the large intestine for medical inspection.

2. Related Art Statement

Recently, there has been an extensive use of an endoscope whereby organs within a body cavity can be observed by inserting an elongated insertable part into the body cavity and various curing treatments can be made by using treatment tools inserted through a treating tool channel as required.

Now, in the conventional endoscope inspection, the doctor judges the advancing direction of the endoscope (insertable part) by observing the endoscope image while inserting the endoscope.

However, a high technique and skill are required to insert an endoscope in inspecting the large intestine.

OBJECT AND SUMMARY OF THE INVENTION

An object of the present invention is to provide an endoscope insertion direction detecting method whereby the endoscope insertion direction can be simply detected.

Another object of the present invention is to provide an endoscope insertion direction detecting mentod whereby the endoscope insertion direction can be detected simply within a short time.

Further another object of the present invention is to provide an endoscope insertion direction detecting method whereby such influence as of noise can be reduced and the endoscope insertion direction can be detected more accurately.

The endoscope insertion direction detecting method of the present invention is to extract the form of a fold existing on the inside wall of an observed part from an endoscope picture image and to judge the endoscope insertion direction on the basis of the form of this fold. It comprises, for example, a step of extracting discontinuous points in an endoscope picture image, a step of extracting line segments based on the above mentioned discontinuous points from respective divided picture images obtained by dividing into a plurality of picture images the picture image obtained by the above mentioned step of extracting the discontinuous points, a step of connecting the line segments obtained by the above mentioned step of extracting the line segments and a step of considering the line connected by the above mentioned connecting step to be the form of a fold existing on the inside wall of the observed part and judging the endoscope insertion direction on the basis of this form of the fold. The above mentioned step of extracting the discontinuous points determines the degree to which the brightness of the picture image varies. The above mentioned step of extracting the line segments has, for example, a step of extracting line segment candidates and a further step of extracting the optimum line segment from among those candidates. For example, the above mentioned step of extracting the candidates includes using a modified Hough transformation in extracting the line segments. The above mentioned step of extracting the optimum line segment includes making a perceptual grouping to extract the optimum line segment. The above mentioned connecting step includes, for example, extracting a search starting line segment by utilizing a pyramid quad tree structure.

The other features and advantages of the present invention will become apparent enough with the following explanation.

BRIEF DESCRIPTION OF THE DRAWINGS

FIG. 23 is a table showing an example of a result of a perceptual grouping.

DETAILED DESCRIPTION OF PREFERRED EMBODIMENTS

First of all, the summary of the present invention shall be explained with reference to FIGS. 2 to 7.

Figure 2:
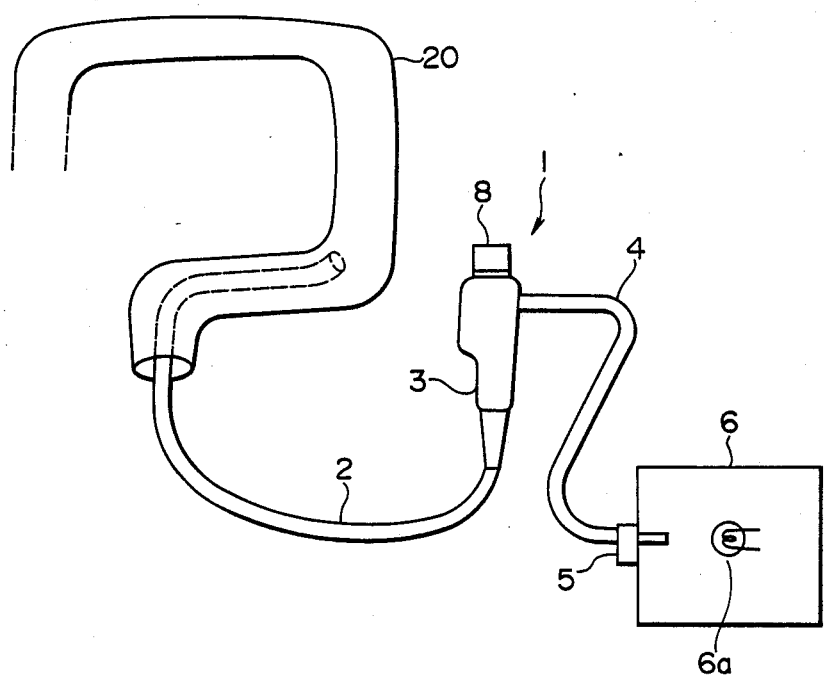
FIG. 2 is an explanatory view showing the insertion of an endoscope into the large intestine.

As shown in FIG. 2, an endoscope (fiber scope) 1 is provided with an elongated flexible insertable part 2 and a thick operating part 3 connected to this insertable part 2 at the rear end. A flexible universal cord 4 is extended sidewise from the above mentioned operating part 3 and is provided at the tip with a connector 5 which is to be connected to a light source apparatus 6. The above mentioned operating part is provided at the rear end with an eyepiece part 8.

As shown in FIG. 2, a rigid tip part 11 and a rearward curvable part 12 adjacent to this tip part 11 are provided in turn on the tip side of the above mentioned insertable part 2. Also, the above mentioned operating part 3 is provided with a curving operation knob not illustrated so that the above mentioned curvable part 12 may be curved vertically and horizontally by rotating this operating knob.

An illuminating lens 15 of an illuminating optical system and an objective lens 16 of an observing optical system are arranged as directed substantially in the same direction in the above mentioned tip part 11. A light guide not illustrated made, for example, of a fiber bundle is provided on the rear end side of the above mentioned illuminating lens 15. This light guide is inserted through the above mentioned insertable part 2, operating part 3 and universal cord 4 and is connected to the above mentioned connector 5 so that, when this connector 5 is connected to the above mentioned light source apparatus 6, an illuminating light emitted out of a lamp 6a within this light source apparatus will enter the above mentioned light guide at the entrance end, will be led to the tip part 11 by the above mentioned light guide, will be emitted out of the tip surface and will be radiated to an object through the above mentioned illuminating lens 15. By the way, in FIG. 3, the reference numeral 17 represents an illuminating range of the illuminating light.

On the other hand, the tip surface of the image, not illustrated, made of a fiber bundle is arranged in the image forming position of the above mentioned objective lens 16. This image guide is inserted through the above mentioned insertable part 2 and is extended to the above mentioned eyepiece part 8. The object image formed by the above mentioned objective lens 16 will be led to the above mentioned eyepiece part 8 and will be observed through an eyepiece lens, not illustrated, which is mounted in the eyepiece part 8. By the way, in FIG. 3, the reference numeral 18 represents a visual field range of the observing optical system.

Figure 3:
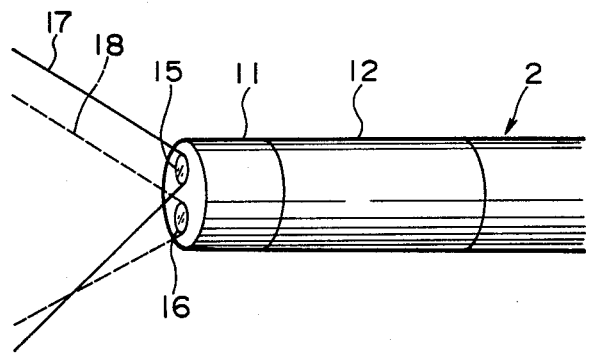
FIG. 3 is a perspective view showing the tip part of an endoscope insertable part.

Now, as shown in FIG. 3, the illuminating optical system and observing optical system of the endoscope 1 are adjacent to each other and are directed substantially in the same direction.

On the other hand, annular folds (called also haustras) exist on the inside wall of the large intestine. Most endoscope doctors judge the endoscope insertion direction by the manner in which such an annular fold is seen. That is to say, the center of the ring of such fold is an excellent cirterion in judging the endoscope insertion direction. This shall be explained with reference to FIGS. 4 to 7.

Figure 5:
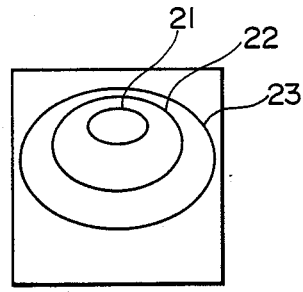
FIG. 5 is an explanatory view showing an endoscope image in the state of FIG. 4.
Figure 7:
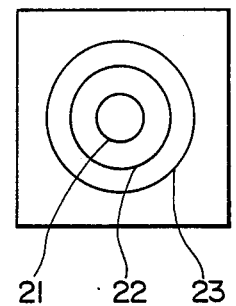
FIG. 7 is an explanatory view showing an endoscope image in the state of FIG. 6.

By the way, in FIGS. 5 and 7, the reference numerals 21 and 22 represent folds existing on the inside wall of the large intestine.

Figure 4:
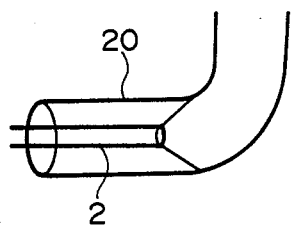
FIG. 4 is an explanatory view showing the insertion of an endoscope into a bent part of the large intestine.

FIG. 4 shows the case of inserting the insertable part 2 of the endoscope 1 into an upward bent part of the large intestine. In such case, as shown in FIG. 5, the folds exist as deviated upward. Therefore, in this case, the tip part 11 of the endoscope 1 may be curved upward and the insertable part 2 may be inserted upward.

Figure 6:
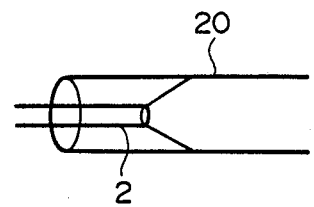
FIG. 6 is an explanatory view showing the insertion of an endoscope into a straight part of the large intestine.

FIG. 6 shows the case of inserting the insertable part 2 of the endoscope 1 into a straight part of the large intestine 20. In this case, as shown in FIG. 7, the folds exist without deviating vertically or horizontally. Therefore, in this case, the insertable part 2 of the endoscope 1 may be inserted straight as it is.

Thus, in the endoscope insertion direction detecting methnod, the form of the folds existing on the inside wall in the endoscope image is extracted and the endoscope insertion direction is detected on the basis of the form of these folds.

Figure 8:
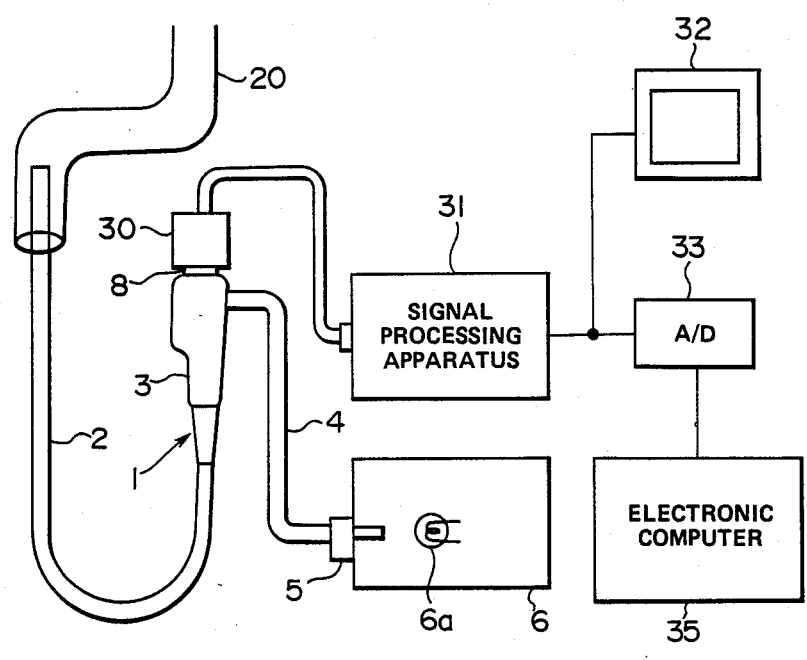
FIG. 8 is an explanatory view showing an example of an endoscope apparatus using a fiber scope and externally fitted television camera.
Figure 9:
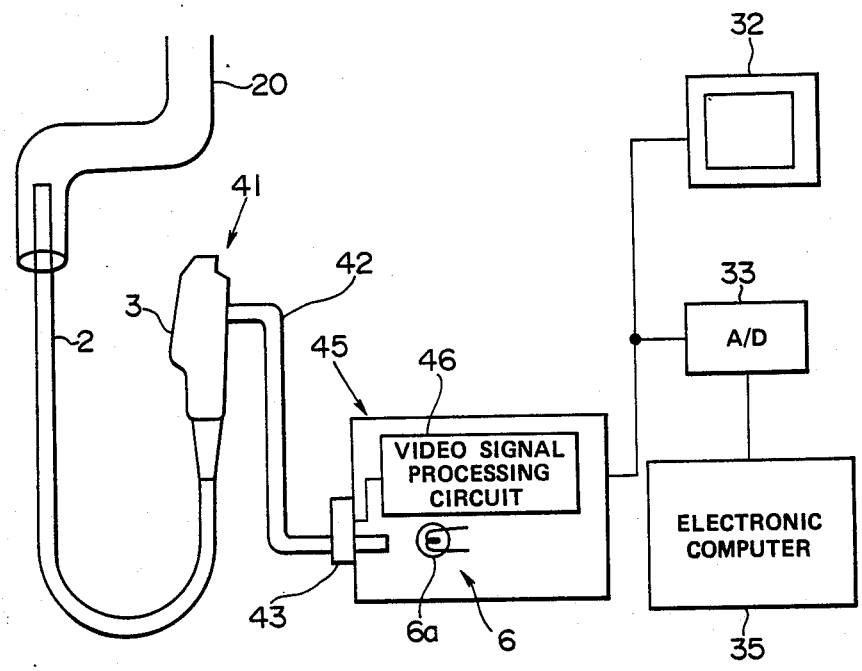
FIG. 9 is an explanatory view showing an example of an endoscope apparatus using a video scope.

The endoscope insertion direction detecting method of this embodiment is applied to an endoscope apparatus shown, for example, in FIG. 8 or 9.

The endoscope apparatus shown in FIG. 8 is provided with a fiber scope 1 fed with an illuminating light by a light source apparatus 6 and an externally fitted television camera 30 fitted to an eyepiece part 8 of this fiber scope 1. The formation of the above mentioned fiber scope 1 is the same as is shown in FIG. 2 and shall not be explained here. The above mentioned externally fitted television camera 30 is provided, for example, with an image lens not illustrated forming an image of a light from the above mentioned eyepiece part 8 and a solid state imaging device, not illustrated, arranged in the image plane of this image forming lens. This externally fitted television camera 30 drives the above mentioned solid state imaging device and is to be connected to a signal processing apparatus processing the output signal of this solid state imaging device to be a video signal. The video signal output out of the above mentioned signal processing apparatus 31 will be input into a monitor 32, will be converted to a digital form by an A/D converter 33, will be then input into an electronic computer 35 and will be taken into a memory not illustrated within this electronic computer 35. The endoscope image will be displayed in the above mentioned monitor 32 and the endoscope insertion direction detecting method in this embodiment will be carried out by the above mentioned electronic computer 35.

The endoscope apparatus shown in FIG. 9 is provided with a video scope 41 instead of the fiber scope 1 and externally fitted television camera 30. The same as in the above mentioned fiber scope 1, this video scope 41 is provided with an elongated flexible insertable part 2 and an operating part 3 connected to this insertable part 2 at the rear end. A flexible universal cord 42 is extended sidewise from the above mentioned operating part 3 and is provided at the tip with a connector 43 which is to be connected to a control apparatus 45 containing a light source apparatus 6 and video signal processing circuit 46. A solid state imaging device not illustrated is arranged in the image forming position of the objective lens in the tip part of the insertable part 2 of the above mentioned video scope 41 and is connected to a video signal processing circuit 46 within the above mentioned control apparatus 45 through the signal lines inserted through the above mentioned insertable part 2, operating part 3 and universal cord 42 and the above mentioned connector 43. By the way, the illuminating optical system of the above mentioned video scope 41 is the same as of the fiber scope 1 in that the illuminating light emitted from the lamp 6a of the light source apparatus 6 within the above mentioned control apparatus 45 may enter the light guuide at the entrance end. The above mentioned solid state imaging device will be driven by the above mentioned video signal processing circuit 46 and the output signal of this solid state imaging device will be processed to be a video signal by the above mentioned video signal processing circuit. The same as in the endoscope apparatus using the fiber scope 1, the video signal output from this signal processing circuit 46 will be input into the monitor 32, will be converted to be of a digital amount by the A/D converter 33, will be then input into the electronic computer 35 and will be taken into the memory not illustrated within this electronic computer 35. The endoscope image will be displayed in the above mentioned monitor 32 and the endoscope insertion direction detecting method in this embodiment will be carried out by the above mentioned electronic computer 35.

Figure 1:
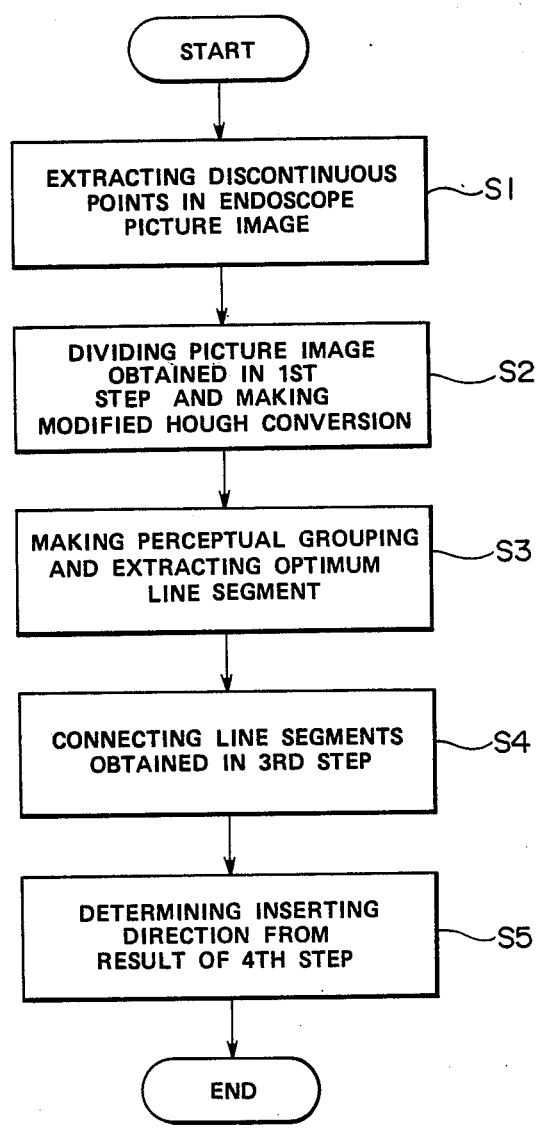
FIG. 1 is a flow chart showing a method of an embodiment of the present invention.

The endoscope insertion direction detecting method in this embodiment shall be explained in the following. As shown in the flow chart in FIG. 1, the endoscope insertion direction detecting method of this embodiment comprises a first step S1 of extracting discontinuous points in an original picture taken into the electronic computer 35, a second step S2 of dividing the picture image obtained in the above mentioned first step S1 into a plurality of picture images and extracting line segment candidates by using a modified Hough conversion from each of the divided picture images, a third step S3 of perceptually grouping the line segment candidates obtained in the above mentioned second step and extracting the optimum line segment from each of the divided picture images, a fourth step S4 of connecting the line segments obtained in the above mentioned third step S3 and a fifth step S5 of determining the insertion direction from the result of the above mentioned fourth step S4.

First of all, the first step shall be explained with reference to FIGS. 10 to 11.

In extracting discontinuous points, a color consisting of a red intensity, a green intensity and a blue intensity may be noted or a gray level (thickness or brightness) may be noted. In this embodiment, the case of noting a gray level shall be explained. The number of pixels of the original picture shall be $512 \times 512$ and the gray level shall be of 256 gradations.

Extracting discontinuous points by noting a gray level is to inspect the variation rate (gradient) of the gray level on a spatial coordinate and extract the gray level in the variation. This is an edge detection by noting the gray level.

As the above mentioned edge detecting method, there is, for example, a spatial filtering by using an overlapped matrix which is used in this embodiment.

A spatial filtering, for example, in the case of using an overlapped matrix consisting of $3 \times 3$ pixels shall be explained with reference to FIG. 10. In FIG. 10, $P_1(x_i,y_i)$ represents a gray level of a pixel of a coordinate $(x_i,y_i)$ of an input picture image $P_1$. In the same manner, $P_2(x_i,y_i)$ represents a gradient of a picture image of a coordinate $(x_i,y_i)$ of an output picture image $P_2$.

First of all, the vicinity of $3 \times 3$ of the input picture image $P_1(x_i,y_i)$ is taken out, a product of the value of each pixel of the vicinity of $3 \times 3$ and the value of each element corresponding to the overlapped matrix consisting of separately prepared $3 \times 3$ elements is calculated to determine a sum of 9 products to be $P_2(x_i,y_i)$.

This operation is made in turn for the respective pixels of the input picture image to obtain an output picture image $P_2$ to which a spatial filtering has been applied.

Figures 10, 11A, 11B:
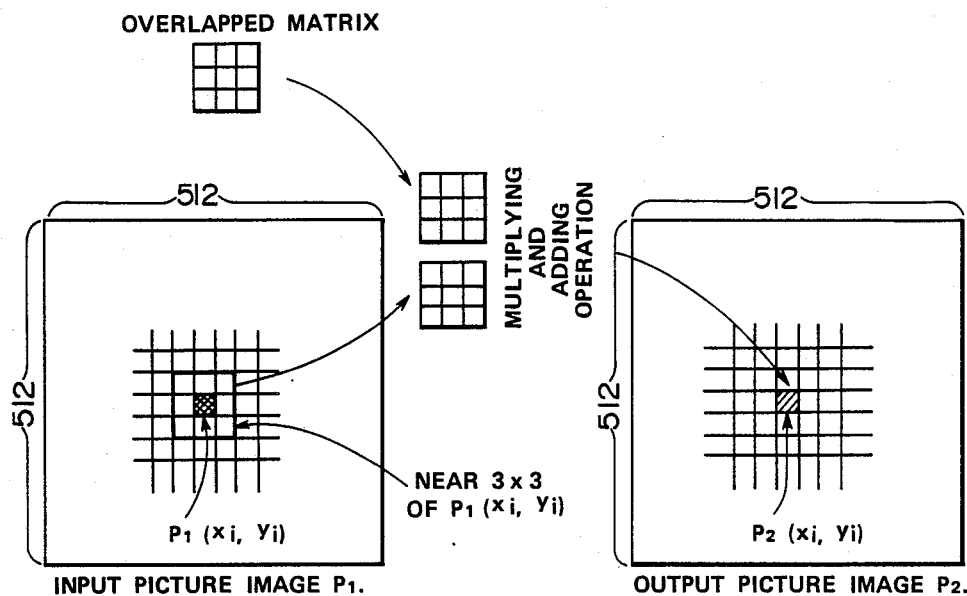
FIG. 10 is a view for explaining the use of a spatial filtering in the first step.
FIG. 11(a) is an explanatory view showing an overlapped matrix determining a gradient in an x-direction.
FIG. 11(b) is an explanatory view showing an overlapped matrix determining a gradient in a y-direction.

Now, a gradient (gray level variation rate) $g_x$ in the x-direction is obtained by using an overlapped matrix shown in FIG. 11(a). In the same manner, a gradient (gray level variation rate) $g_y$ in the y-direction is obtained by using an overlapped matrix shown in FIG. 11(b). An absolute value of the gradient in some pixel is given by the below mentioned formula (1-1) but, in this embodiment, the absolute value need not be very accurate and therefore, for the brevity of the operation process, it may be approximated by the formula (1-2):

$$g = \sqrt{g_x^2 + g_y^2} \qquad (1\text{-}1)$$

$$g = |g_x| + |g_y| \qquad (1\text{-}2)$$

where g represents the intensity of the discontinuity.

By the way, $g_x$ and $g_r$ of the pixel of the coordinate $(x_i,y_i)$ in case the overlapped matrices shown in FIGS. 11(a) and 11(b) are used are given concretely by the below mentioned formulae (1-3) and (1-4):

$$\begin{aligned}
g_x &= P_2(x_i,y_i) \\
&= -P_1(x_{i-1},y_{i+1}) + \\
&\quad P_1(x_{i+1},y_{i+1}) - \\
&\quad \sqrt{2} \cdot P_1(x_{i-1},y_i) + \\
&\quad \sqrt{2} \cdot P_1(x_{i+1} + y_i) - \\
&\quad P_1(x_{i-1},y_{i-1}) + \\
&\quad P_1(x_{i+1} + y_{i-1})
\end{aligned} \qquad (1\text{-}3)$$

$$\begin{aligned}
g_y &= P_2(x_i,y_i) \\
&= P_1(x_{i-1},y_{i+1}) + \\
&\quad \sqrt{2} \cdot P_1(x_i + y_{i+1}) + \\
&\quad P_1(x_{i+1} + y_{i+1}) - \\
&\quad P_1(x_{i-1} + y_{i-1} -) \\
&\quad \sqrt{2} \cdot P_{11}(x_i,y_{i-1}) - \\
&\quad P_1(x_{i+1} + y_{i-1}).
\end{aligned} \qquad (1\text{-}4)$$

The direction of the edge is given by the following formula (1-5):

$$\theta = \arctan(g_y/g_x) \qquad (1\text{-}5).$$

Here, g determined by the formula (1-1) or (1-2) is compared with a predetermined reference value $g_r$ and edge points above the reference value $g_r$ are left.

It can be considered to reduce the number of the left edge points by setting the reference value $g_r$ to be a large value but, if the reference value $g_r$ is set to be a too large value, inherently necessary edge points will be likely to be removed and therefore it is important to set $g_r$ to be rather low. It is preferable to set the reference value $g_r$ so as to leave about 80% of all the edge points. It may be set so that about 80% of the edge points may remain after the dispersion of g of all the edge points is determined.

Thus, when the somewhat small value of $g_r$ is is used and then the perceptual grouping is made, a weak but significant edge point will be able to be extracted without being influenced by noise or the like. This is one of the features of this embodiment.

The second step shall be explained in the following with reference to FIGS. 12 to 19.

Figure 12:
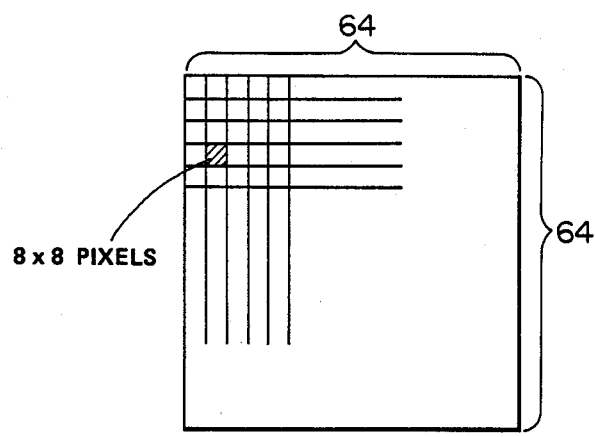
FIG. 12 is an explanatory view showing a picture image obtained in the first step as divided into small squares of 8×8 pixels.

First of all, as shown in FIG. 12, the output picture image $P_2(x_i, y_i)$ obtained in the first step is divided into small squares of about $8 \times 8$ pixels and is modified-Hough-converted. In case the original picture image consists of $512 \times 512$ pixels, it will be divided into $64 \times 64$ picture images. By the way, in this embodiment, for example, it is divided into small squares of $8 \times 8$ pixels but, depending on the required precision, it may be divided into $4 \times 4$ pixels and others.

Figure 13:
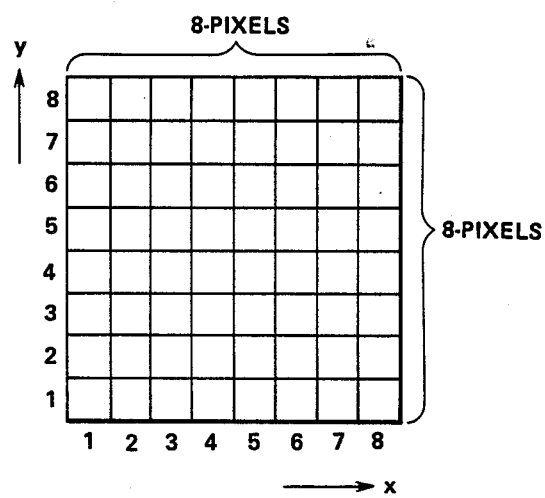
FIG. 13 is an explanatory view showing a small square of 8×8 pixels.
Figure 14:
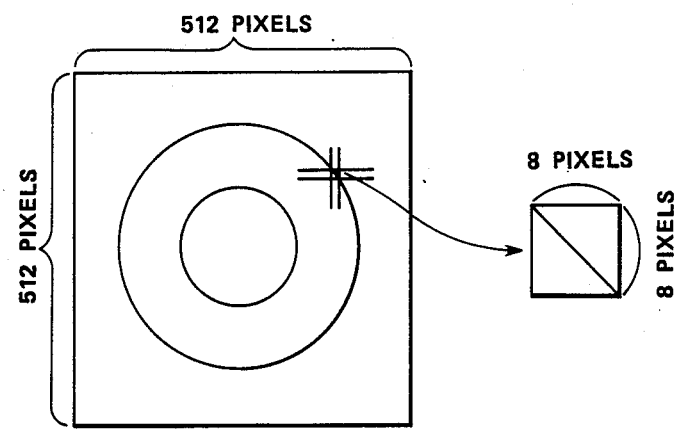
FIG. 14 is an explanatory view showing a line segment of a fold located in a small region of 8×8 pixels.

An output picture image $P_2(x_i, y_i)$ and a cut out small square of $8 \times 8$ pixels are shown respectively in FIGS. 12 and 13. By the way, as shown in FIG. 14, when a small square of $4 \times 4$ to $16 \times 16$ pixels is cut out, the fold in the small square will be able to be considered to be substantially a straight line.

First of all, the modified Hough convnersion shall be briefly explained.

Figure 15:
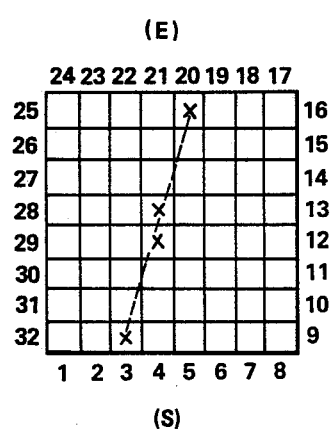
FIG. 15 is an explanatory view showing a small square of 8×8 pixels fitted on the outer periphery with addresses to make a modified Hough transformation.

FIG. 13 is expressed by a commonly well used x,y coordinate system. In order to make a modified Hough conversion, as shown in FIG. 15, addresses are attached to the outer periphery of the small square of $8 \times 8$ pixels.

Then, the straight line on the small square of $8 \times 8$ pixels can be defined by designating a starting address (S) and ending address (E). For example, the straight line represented by the broken line in FIG. 15 can be defined as a straight line of a starting address of 3 and ending address of 20.

On the other hand, the kinds of straight lines which can be described on the small square of $8 \times 8$ pixels are $(32 \times 32)/2 = 512$. The reason for multiplying $(32 \times 32)$ by ½ is that the straight line on the small square is not a vector. That is to say, because the straight line of the starting address of 3 and ending address 20 and the straight line of the starting address 20 and ending address of 3 can be considered to be identical with each other.

Figure 16:
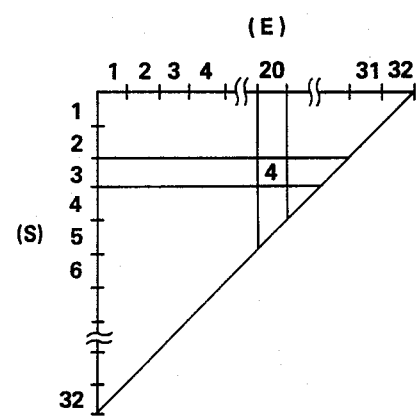
FIG. 16 is an explananatory view showing arranged elements obtained by modified-Hough-converting straight lines.

Therefore, all the straight lines correspond to one of the arranged elements in FIG. 16.

When any edge points on the straight line corresponding to one arrangement on the arranged elements are expressed on the arranged elements, for example, the straight line shown by the broken line in FIG. 15 will be a straight line of a starting address of 3 and ending address of 20, will have four edge points on it and therefore will be expressed as in FIG. 16.

Figures 17, 18:
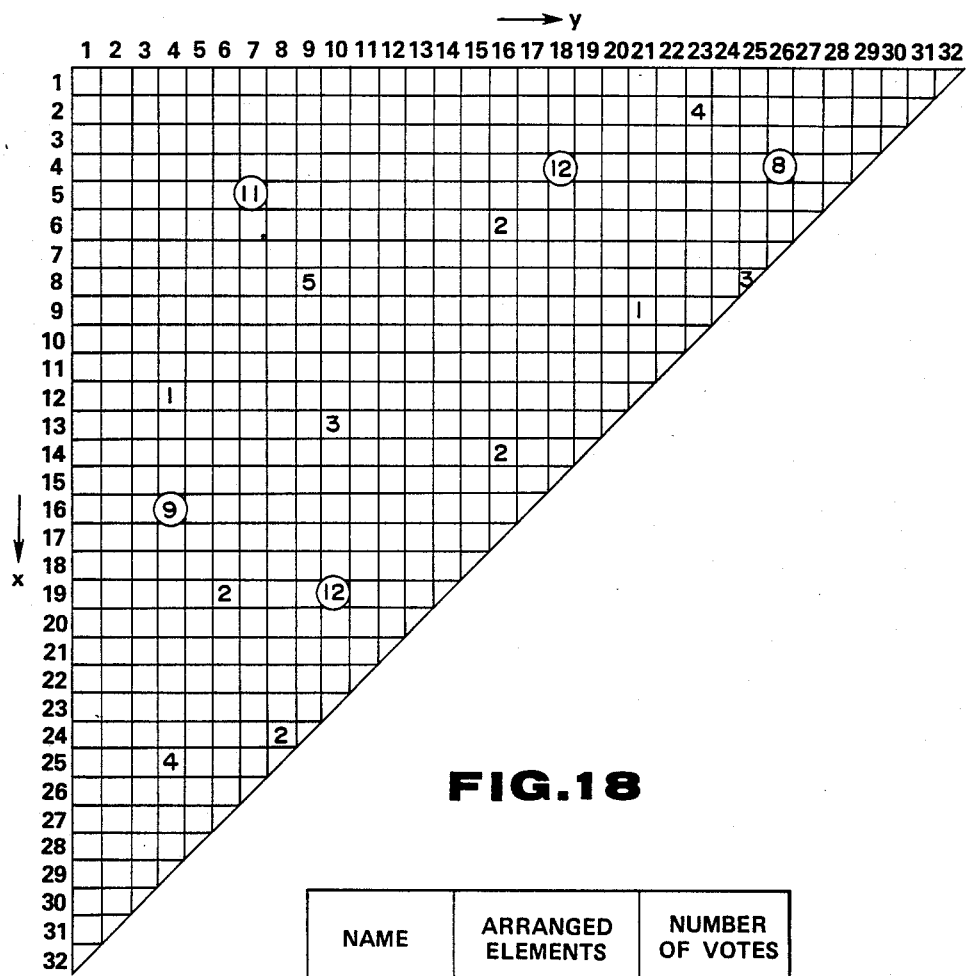
FIG. 17 is an explanatory view showing arranged elements obtained by modified-Hough-converting straight lines and an example of a number of edge points located on straight lines corresponding to the respective arranged elements.
FIG. 18 is a table showing straight lines of a large number of edge points.

If a modified Hough transformation is made along such idea, in fact, such result as is shown in FIG. 17 will be obtained. As already described, one of the arranged elements (one of the squares in FIG. 17) corresponds to one straight line and the numeral (vote) within the arranged element represents the number of edge points existing on the straight line.

The larger the number of the edge points existing on the straight line, the higher the possibility of the straight line to be the required straight line.

Therefore, about 5 votes are extracted as line segment candidates from the larger number of votes. Such extracted line bears à mark ○ in FIG. 17 and is shown in a table in FIG. 18.

By the way, here is an idea of extracting the largest number of votes and making it a required line segment. However, if it is made so, a wrong line segment will be likely to be extracted, for example, as in the case shown in FIG. 19 in which, though (a) is a line segment wanted to be extracted, if judged only by the number of votes, the line segment of (b) will be erroneously extracted.

In order to avoid such danger as is mentioned above, here the number of votes is reduced to about 5 arranged elements, finally a perpetual grouping is made and the optimum line segment is extracted.

The perceptual grouping of the third step shall be explained in the following with reference to FIGS. 20 to 23.

In this embodiment, the perceptual grouping is made by noting the below mentioned three items. However, in addition to the below mentioned three items, the size of the gradient (edge magnitude) may be noted or the color may be noted.

1. Edge orientation
    (on edge points):
    Reference: $\pm 22.5°$
2. Gray level
    (on pixels):
    Reference: $\pm 4$ level.
3. Continuity
    (on edge points):
    Reference: $\pm 1$ pixel distance.

Each of the above mentioned three items shall be explained in the following:

For example, in the case of FIG. 17, the following processes are made on each of the five lines in FIG. 17:

1. Edge orientation

Figures 19, 20:
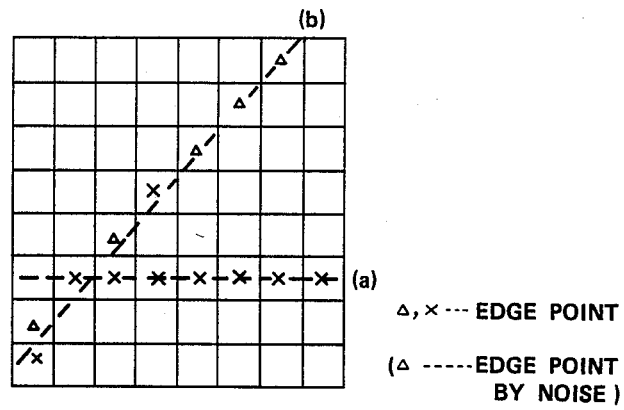
FIG. 19 is an explanatory view showing line segments within a small square.
FIG. 20 is a table showing a grouping by an edge orientation.

For example, in the line 4, that is, of the arranged element (16, 4) in FIG. 18, as shown in FIG. 20, 9 edge points are arranged in the order of the smaller edge direction $\theta$ determined in the first step. A grouping is made where there is a gap larger than 45°. In the example shown in FIG. 20, the difference of $\theta$ between the 8th edge point and 9th edge point is $$62° - 35° = 27° \ (>22.5°).$$

Here, a grouping is made.

2. Gray level

The same as in the case of the above mentioned edge orientation, the gray levels of the parts corresponding to the edge points are arranged in the order of the smaller one and a grouping is made where the gap of the gray levels is larger than 4.

3. Continuity

Figures 21, 22:
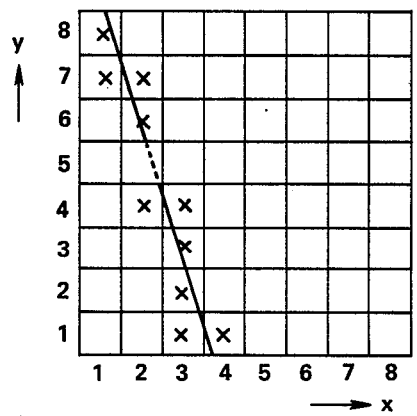
FIG. 21 is a table showing a grouping by a continuity.
FIG. 22 is an explanatory view showing edge points on a small square for explaining a grouping by a continuity.

The x-coordinates and y-coordinate of the edge points are noted and are arranged in the order of the smaller x-coordinate as shown in FIG. 21. The same x-coordinates are arranged in the order of the larger y-coordinate. Where the difference Δx of the x-coordinate is Δx>1 or the difference Δy of the y-coordinate is Δy>1, a grouping is made. In the example in FIG. 21, the difference of the y-coordinate between the 4th edge point and 5th edge point is 2 and here a grouping is made. Thus, by noting both of the x-coordinate and y-coordinate, even if the straight line extremely rises or lies with respect to the x-axis or y-axis, the discontinuous point can be positively extracted and a grouping can be made. For example, in FIG. 22, the respective edge points in the example in FIG. 21 are plotted on the x- and y-coordinates. In such case, if only the x-coordinate is noted, it can not be detected that the straight line is discontinuous.

By making the above three operations, generally, such results as are shown, for example, in FIG. 23 are obtained.

Here, for example, if a logical formula of $$\text{Continuity} \cap \text{(Gray Level)} \cap \text{(Edge Orientation)} \quad (1)$$

is applied as a condition of extracting the optimum line segment, as shown in FIG. 23, the edge points can be grouped in six groups of A to F. In the example in FIG. 23, the group A has the most edge points and the number of the edge points is 6.

By the way, the condition of extracting the optimum line segment is not limited to the logical formula (1) but, for example, the following logical formula (2) may be used:

$$\text{Continuity} \cap \text{(Gray Level} \uparrow \text{Edge Orientation)} \quad (2).$$

The same is carried out also on the other arranged elements and the group having the most edge points among them is extracted and is a line segment to be extracted in the small square of 8×8 pixels.

Thus, in the third step, a line segment of 64×64 small regions consisting of 8×8 pixels could be extracted. (Needless to say, there are many small regions in which no line segment exists.) By the way, by the division into small regions, there are advantages that parallel processes by a plurality of computers are possible and the operating time can be reduced. By the way, parallel processes may be made by using a plurality of exclusive IC's.

By the way, also in the case of noting the size of the gradient (edge magnitude) or the color, in the same manner, the edge points may be arranged in the order of the size of the gradient or the color and may be grouped where there is a gap larger than is predetermined.

The fourth step shall be explained in the following with reference to FIGS. 24 to 26.

In this fouth step, the line segments obtained in the third step are connected. This is called a tracing or connecting of edges.

In tracing the edges, from what segment the tracing is to be started is important. In this embodiment, a pyramid quad tree structure is utilized to trace the edges. A step of obtaining a curve of a fold by utilizing this pyramid quad tree structure shall be explained in the following with reference to FIGS. 24 and 25.

Figure 24:
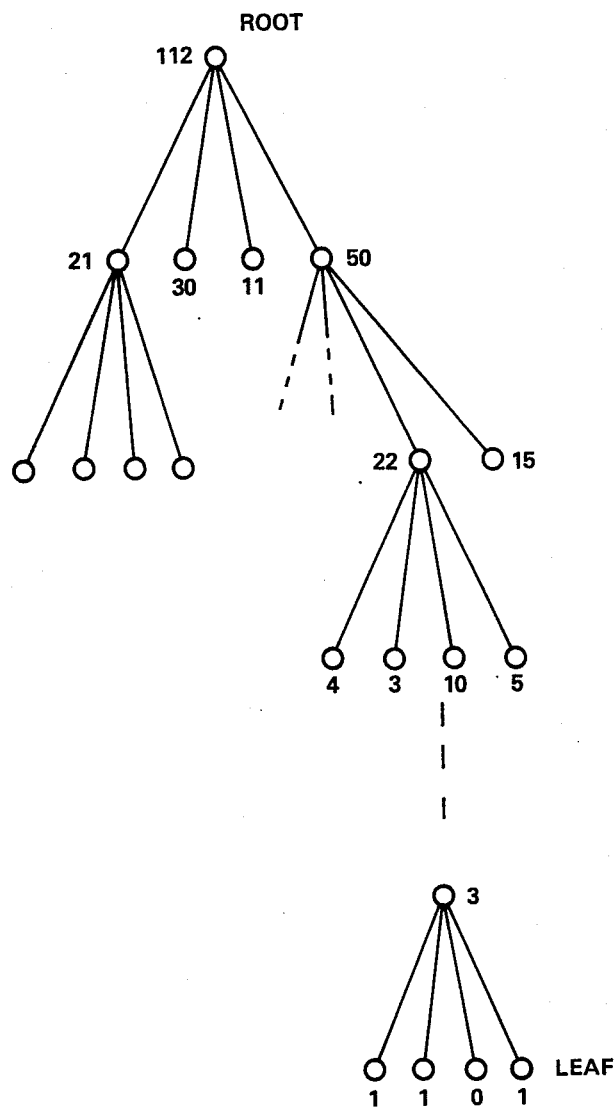
FIG. 24 is an explanatory view showing a pyramid quad tree structure.
Figure 25:
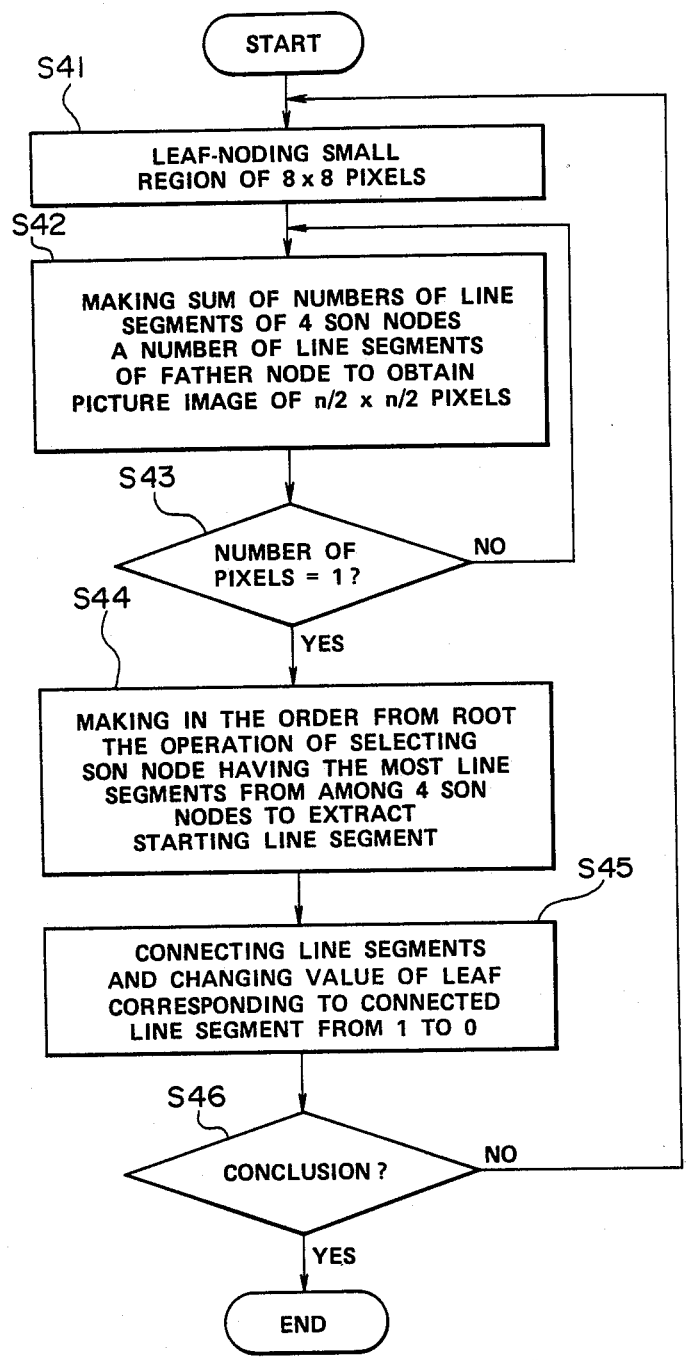
FIG. 25 is a flow chart showinng the fourth step.

First of all, as shown in FIG. 24, a pyramid quad tree structure is made by making a small region consisting of 8×8 pixels a leaf node (or leaf). That is to say, in FIG. 25, in the step S41, a small region of 8×8 pixels is made a leaf node and, in the step S42, the sum of the line segment numbers of four son nodes is made a line segment number of a father node to obtain a picture image of $n/2 \times n/2$ pixels. Then, through the step S43 of judging whether the number of pixels is 1 or not, the step S42 is repeated until a root (or root node) is reached. In the thus made pyramid quad tree structure, the father node retains the number of the line segments of the son nodes. By the way, in FIG. 24, the figures attached near the respective nodes represent the numbers of line segments.

Then, in order to discover a starting line segment, the tree is searched downward from the root, that is to say, in the step S44, the operation of selecting the son node having the most line segments among the four son modes is repeated. As shown in FIG. 24, in the stage of the leaf, in case a plurality of leaves having line segments exist, any line segment may be made a starting line segment.

Then, in the step S45, the line segment determined in the step S44 is made a starting line segment and the line segments are connected.

The operation of connecting these line segments shall be explained with reference to FIGS. 26(a) to (d).

Figure 26A:
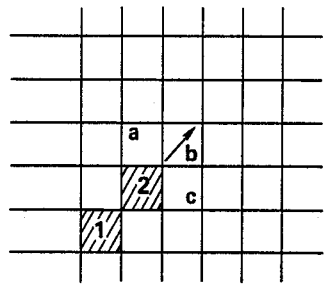
FIGS. 26(a) to (d) are explanatory views showing small squares to be searched next in the case of connecting line segments.

As shown in FIG. 26(a), in case the line segments are connected in the order of the small regions 1 and 2, the next searching direction will be the direction indicated by the arrow in the drawing. Therefore, in this case, the small regions a, b and c are checked.

Figure 26B:
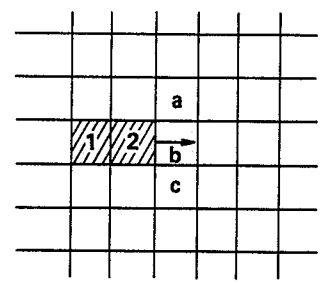

In the same manner, as shown in FIG. 26(b), in case the line segments are connected in the order of the small regions 1 and 2, the next searching direction will be the direction indicated by the arrow in the drawing. In this case, the small regions a, b and c are checked.

Figure 26C:
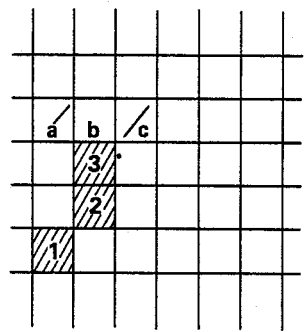

As shown in FIG. 26(c), in case the line segments are connected in the order of the small regions 1 and 2, the small regions a, b and c are checked but, in case the line segments exist in both of the small regions a and c, the directions of the line segments a and c are checked and the direction in which a smooth connection is made is selected. In the case of FIG. 26(c), the line segment of the small region c is selected.

Figure 26D:
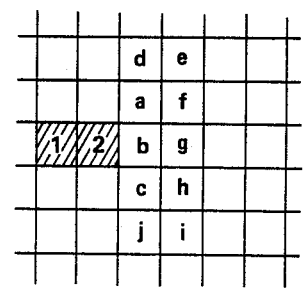

As shown in FIG. 26(d), in case the line segments are connected in the order of the small regions 1 and 2 and no line segment exists in the small regions a, b and c, the small regions d, e, f, g, h, i and j are inspected, because, in case the line segment a is considered to have lapsed for any reason, the next search will be of d, e and f, in the same manner, in case the line segment b is considered to have lapsed, the next search will be of f, g and h and, in case the line segment c is considered to have lapsed, the next search will be of h, i and j.

In case the line segments are to be connected, the angle formed by two line segments to be connected may be limited to be within ±45°.

Whenever the line segments are connected, the numerical value on the quad tree will be corrected. That is to say, the value of the leaf corresponding to the connected line segment will be changed from 1 to 0. The value of the father node above it will be also corrected.

The line segments are connected in both directions.

When a curve is thus obtained, in the step S46, whether the fourth step is to be concluded or not is judged and, in case it is not to be concluded, when the steps in and after the step S41 are again repeated, another curve can be obtained.

The fifth step shall be explained in the following with reference to FIGS. 27 to 31.

In the fifth step, the insertion direction is judged and determined by the form of the fold determined in the fourth step.

The form of the fold to be determined is of such pattern as is shown, for example, in FIGS. 27(a) to (d). The insertion direction is determined respectively by the methods explained in the following.

Figure 27A:
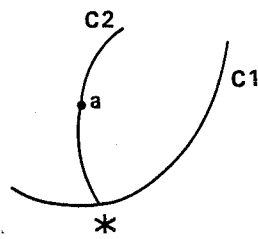
FIGS. 27(a) to (d) are explanantory views showing a method of determining an insertion direction from the form of a fold.

FIG. 27(a) shows the case that two curves (folds) C $C_1$ and $C_2$ having an intersection (or branching point) indicated by the mark * in the drawing are obtained. In this case, by judging the direction of the line segment at the point indicated by the mark * in the drawing, which fold is inner is judged. In the case of FIG. 27(a), the curve $C_2$ is inner and the center (point a) of the inner curve is made an insertion direction. By the way, the case that such curve is obtained is considered to be a case that, as such tube cavity as of the large intestine in which an endoscope is inserted is curved, the inner fold is partly hidden.

Figure 27B:
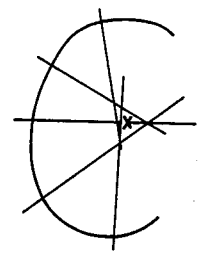

In the method shown in FIG. 27(b), radial lines are constructed respectively at about five points on the obtained curve and the part in which the intersections of the radial lines concentrate is made the insertion direction.

Figure 27C:
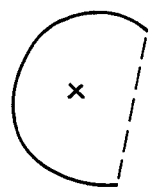
Figure 27D:
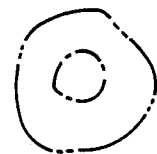

In the method shown in FIG. 27(d), in case the obtained curve is broken anywhere, the nearest curves are connected and the center of gravity of the obtained ring is made an insertion direction.

By the way, in the methods shown in FIGS. 27(b) to (d), any curves or rings may be used, the largest curve or ring may be used or the ring n-th from a large ring may be predetermined to be used.

Figure 28:
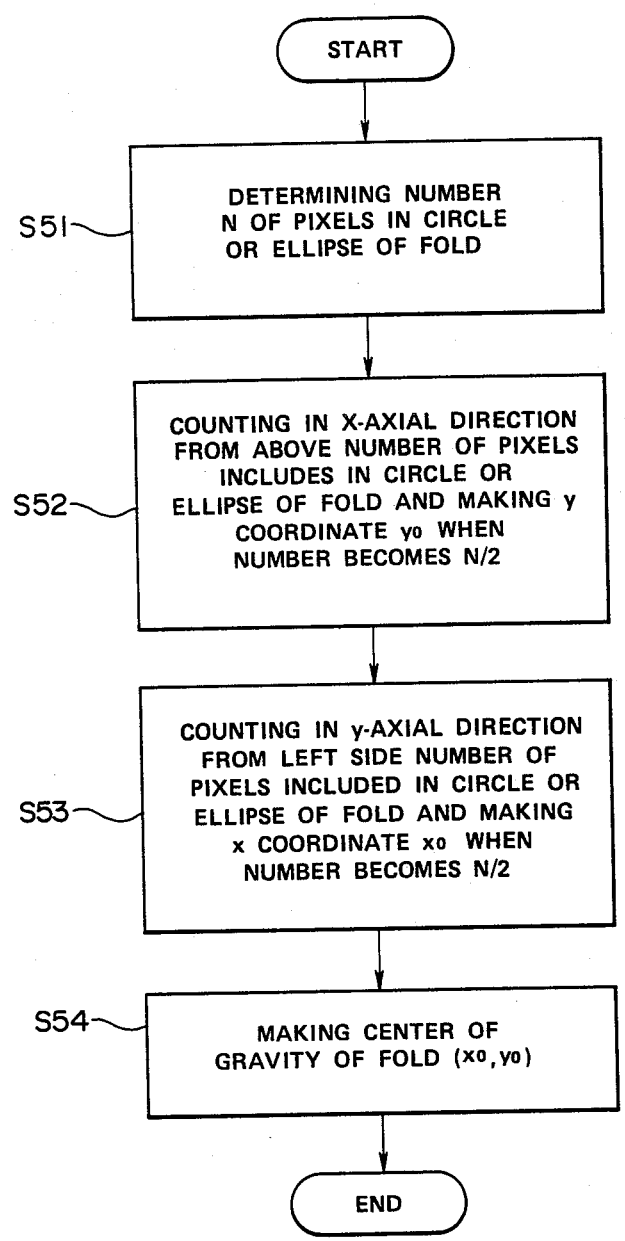
FIG. 28 is a flow chart showing a step of determining the center of gravity of a ring.

The center of gravity can be determined by such process as is shown, for example, in FIG. 28.

Figure 29:
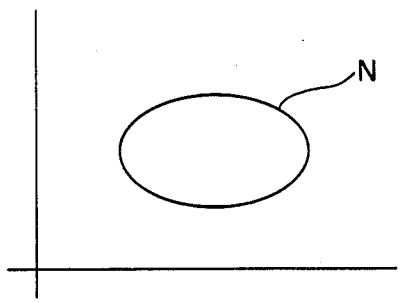
FIG. 29 is an explanatory view showing an ellipse of a foil.

First of all, in the step S51, the number of pixels contained in the circle or ellipse of a fold is determined and is made N as shown in FIG. 29. By the way, the number of pixels may be replaced with the number of small squares used in the step.

Figure 30:
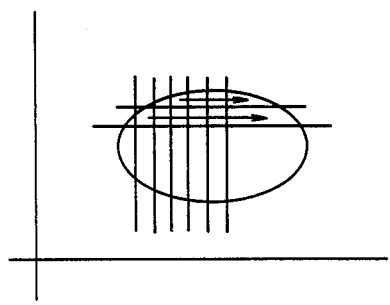
FIG. 30 is an explanatory view showing a step of determining an x-coordinate of the center of gravity of a ring.

Then, in the step S52, as indicated by the arrows in FIG. 30, the number of pixels contained in the circle or ellipse of the fold is counted in the direction of the x-axis from above until the number becomes N/2. The value of the y-coordinate when the number becomes N/2 is represented by $y_0$ which is a y-coordinate of the determined center of gravity.

Figure 31:
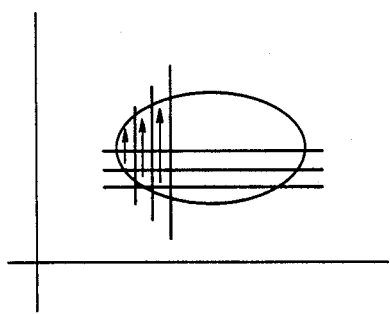
FIG. 31 is an explanatory view showing a step of determining a y-coordinate of the center of gravity of a ring.

In the same manner, in the step S53, as indicated by the arrows in FIG. 31, the number of pixels contained in the circle or ellipse of a fold is counted in the direction of the y-axis from the left side until the number N/2. The value of the x-coordinate when the number becomes N/2 is representedd by $x_0$ which is an x-coordinate of the determined center of gravity.

Then, in the step S54, the center of gravity of the fold is determined as $(x_0, y_0)$. By the way, the form of the fold has been explained to be circular or elliptic but is not limited to be such.

By the way, as the endoscope is inserted, the form of the fold will vary. Therefore, the center of gravity of the fold n-th as counted from a large one may be always determined and may be judged to be an insertion direction or an average value of the center of gravity of the fold n-th as counted from a large one and the center of gravity of the n+m-th fold may be determined and may be judged to be an insertion direction. Also, the center of gravity of the fold on the innermost side may be made an insertion direction. The direction in which the most centers of gravity among centers of gravity of a plurality of folds are located may be made an insertion direction.

By the way, as shown in FIG. 4, in case the large intestine 20 is curved, as shown in FIG. 5, the center of gravity of the fold is different depending on the fold. In the case of FIG. 5, the more on the inside the fold, the more on the upper side, that is, on the insertion direction side the center of gravity. The larger the curvature, the larger the displacement of this center of gravity. Therefore, the curvature of the large intestine 20 can be detected from the displacements of the centers of gravity of a plurality of folds.

Thus, according to this embodiment, the form of a fold is determined by the first to fourth steps, the endoscope insertion direction is judged in the fifth step on the basis of the form of the fold and thereby the endoscope insertion direction can be simply detected.

In the case of extracting a discontinuous point (edge point) in the endoscope picture by the first step, when the reference value is set to be rather low and the value of the gradient g is left to be small to some extent, a necessary discontinuous point (edge point) will be able to be extracted without being influenced by noise or the like.

In case line segment candidates are extracted by utilizing a modified Hough conversion in the second step or in case the optimum line segment is extracted from the respective divided picture images by a perceptual grouping in the second step, by dividing the endoscope picture image into small regions, parallel processes by a plurality of computers are possible and the operating time can be reduced.

As a pyramid quad tree structure is utilized in extracting a starting line segment in the fourth step, the processing time can be remarkably reduced.

By the way, in this embodiment, a gray level is noted in extracting discontinuous points in the first step but a color may be noted as described above.

In case a color is noted, for example, the variation rates of the hue and saturation may be inspected and the hue and saturation as varying may be extracted.

For example, in case three primary color components (three exciting values) R, G and B of a CIE-RGB coloring system are obtained from an original picture, a hue θ can be represented by the formula (2-2) by using the following formula (2-1):

$$\theta = \cos^{-1} \frac{2r - g - b}{\sqrt{6} \, [(r - 1/3)^2 + (g - 1/3)^2 + (b - 1/3)^2]} \quad (2\text{-}1)$$

$$\theta = \theta_1 \ (g \geq b), \ \theta = 2\pi - \theta_1 \ (g < b) \quad (2\text{-}2)$$

where
r = R/(R+G+B).
g = G/(R+G+B).
b = B/(R+G+B).

The saturation S can be represented by the formula (2-3):

$$S = 1 - 3 \min(r, g, b) \quad (2\text{-}3)$$

By the way, min (r, g, b) represents the minimum value of r, g, b.

Thus, when the hue and saturation are made numerical values for respective pixels of the original picture, the same as in the case of noting the gray level, by a spatial filtering or the like, the hue and saturation as varying can be extracted. The same as in the case of noting a gray level, by carrying out the second to fifth steps, the fold can be extracted by noting the color.

In case the original picture is given by an NTSC signal, the hue can be obtained from the phase of a chrominance signal and the saturation can be obtained from the amplitude of the chrominance signal.

Also, the value of a specific color component may be noted.

By the way, the endoscope operator may insert the endoscope by the curving operation in the endoscope insertion direction detected by the method of the present invention or endoscope may be inserted by automatically directing the tip part by the apparatus.

As explained above, according to the present invention, by extracting the form of a fold and judging on the basis of this form of the fold, there is an effect that the endoscope insertion direction can be simply detected.

Also, by dividing an endoscope picture image into small regions in extracting line segments and by utilizing a pyramid quad tree structure in connecting the line segments, there is an effect of reducing the processing time.

In the case of extracting discontinuous points in an endoscope picture image, by setting the reference value to be rather low, extracting line segment candidates and then extracting the optimum line segment by a perceptual grouping, there are the effects that the influence of noise or the like can be reduced, the form of the fold can be extracted more accurately and the insertion direction can be detected.

It is apparent that, in this invention, implementation methods different in a wide range can be formed without departing from the spirit and scope of the invention. This invention is not restricted by its specific working modes except being limited by the appended claims.

What is claimed is:

1. An endoscope insertion direction detecting method provided with a step of extracting the form of a fold existing on the inside wall of an observed part from an endoscope picture image so that the endoscope insertion direction may be judged on the basis of the form of the fold extracted by said step.

2. An endoscope insertion direction detecting method according to claim 1 wherein said fold form extracting step is to detect a part in which the brightness or color of the picture image varies and to consider said part to be a fold.

3. An endoscope insertion direction detecting method comprising the respective steps of:
   extracting discontinuous points in an endoscope picture image;
   extracting line segments based on said discontinuous points from respective divided picture images obtained by dividing into a plurality of picture images the picture image obtained by said discontinuous point extracting step;
   connecting the line segments obtained by said line segment extracting step; and
   considering the line connected by said connecting step to be the form of a fold existing on the inside wall of an observed part and judging the endoscope insertion direction on the basis of said form of the fold.

4. An endoscope insertion direction detecting method according to claim 3 wherein said discontinuous point extracting step includes extracting points at which the brightness of the picture image varies.

5. An endoscope insertion direction detecting method according to claim 3 wherein said discontinuous point extracting step includes extracting points at which the color of the picture image varies.

6. An endoscope insertion direction detecting method according to claim 3 wherein said discontinuous point extracting step includes extracting discontinuous points by applying a spatial fitering by using an overlapped matrix.

7. An endoscope insertion direction detecting method according to claim 3 wherein said connecting step includes extracting a search starting line segment by utilizing a pyramid quad tree structure in connecting said line segments.

8. An endoscope insertion direction detecting method according to claim 3 wherein said connecting step includes determining the next searched divided picture image in response to the arranging direction of the divided picture images having so far connected line segments.

9. An endoscope insertion direction detecting methnod according to claim 3 wherein said connecting step includes limiting the angle formed by two connected line segments to be within ±45° in connecting said line segments.

10. An endoscope insertion direction detecting method according to claim 3 wherein said endoscope insertion direction judging step includes, in the case that two curves having an intersection are obtained by said connecting step, judging the direction of the line segment at said intersection, thereby judging which curve is inner and then judging the center of the inner curve to be the insertion direction.

11. An endoscope insertion direction detecting method according to claim 3 wherein said endoscope insertion direction judging step includes, in the case that a ring-like line is obtained by said connecting step, judging the center of gravity of said ring-like line to be the insertion direction.

12. An endoscope insertion direction detecting method according to claim 3 wherein said endoscope insertion direction judging step includes judging the part in which concnetrate the intersections of radial lines erected respectively from a plurality of points on the curves obtained by said connecting step to be the insertion direction.

13. An endoscope insertion direction detecting method according to claim 3 wherein said endoscope insertion direction judging step includes, in the case that the curve obtained by said connecting step is like a partly incised ring, connecting the obtained curve at both ends and judging the center of gravity of the thereby obtained ring to be the insetion direction.

14. An endoscope insertion direction detecting method according to claim 3 wherein said endoscope insertion direction judging step includes, in the case that the curve obtained by said connecting step is partly broken, connecting the nearest curves and judging the centger of gravity of the obtained ring to be the insertion direction.

15. An endoscope insertion direction detecting method according to claim 1 or 3 wherein said endoscope picture image is obtained by a television camera fitted to the endoscope eyepiece part capable of naked eye observation.

16. An endoscope insertion direction detecting method according to claim 1 or 3 wherein said endoscope picture image is obtained by an imaging means provided in the endoscope.

17. An endoscope insertion direction detecting mrthod according to claim 3 wherein said line segment extracting step has a step of extracting line segment candidates and a step of extracting the optimum line segment from among the candidates extracted by said candidate extracting step.

18. An endoscope insertion direction detecting method according to claim 17 wherein said candidate extracting step includes using a modified Hough conversion in extracting the line segments.

19. An endoscope insertion direction detecting method according to claim 18 wherein said modified Hough conversion includes defining the line segments within the divided picture image by addresses attached to the periphery of the divided picture image.

20. An endoscope insertion direction detecting method according to claim 17 wherein said optimum line segment extracting step includes carrying out a perceptual grouping to extract the optimum line segment.

21. An endoscope insertioon direction detecting method according to claim 20 wherein said optimum line segment extracting step utilizes at least one of an edge orientation, gray level, continuity, edge magnitude and color in carrying out said perceptual grouping.

* * * * *